(12) United States Patent
Nagaoka

(10) Patent No.: US 9,820,654 B2
(45) Date of Patent: Nov. 21, 2017

(54) OBSERVATION DEVICE

(71) Applicant: OLYMPUS CORPORATION, Hachioji-shi, Tokyo (JP)

(72) Inventor: Hideyuki Nagaoka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/582,635

(22) Filed: Apr. 29, 2017

(65) Prior Publication Data
US 2017/0231502 A1 Aug. 17, 2017

Related U.S. Application Data

(63) Continuation of application No. PCT/JP2015/079432, filed on Oct. 19, 2015.

(30) Foreign Application Priority Data

Nov. 20, 2014 (JP) ................. 2014-235625

(51) Int. Cl.
A61B 5/05 (2006.01)
A61B 5/00 (2006.01)
(Continued)

(52) U.S. Cl.
CPC ............ *A61B 5/0084* (2013.01); *A61B 1/051* (2013.01); *A61B 1/07* (2013.01); *A61B 5/72* (2013.01);
(Continued)

(58) Field of Classification Search
CPC ......... A61B 5/0084; A61B 5/72; A61B 1/051; A61B 1/07; A61B 5/742; G02B 5/201;
(Continued)

(56) References Cited

U.S. PATENT DOCUMENTS 8,936,548 B2 * 1/2015 Ozawa ................. A61B 1/0638 600/178
9,526,408 B2 * 12/2016 Yamaguchi ........ A61B 1/00004
(Continued)

FOREIGN PATENT DOCUMENTS

JP 2012170639 A 9/2012
JP 2012228503 A 11/2012
(Continued)

OTHER PUBLICATIONS

International Search Report (ISR) and Written Opinion dated Dec. 28, 2015 issued in International Application No. PCT/JP2015/079432.

Primary Examiner — Joel Lamprecht
(74) Attorney, Agent, or Firm — Holtz, Holtz & Volek PC

(57) ABSTRACT

An observation device includes a light source unit capable of adjusting a quantity of 390-490 nm illuminating light according to a B1 range and a B2 range having a longer wavelength than the B1 range, and an imaging element that images reflected light from a subject irradiated with illuminating light. The light source unit changes the light quantity ratio of the B1 range to the B2 range depending on whether white light imaging is conducted or narrow band imaging is conducted. The imaging element includes RGB color filters arranged according to pixels and the R color filter transmits more light in an R range and the B1 range than light in the second B range and has a spectral characteristic that satisfies a predetermined conditional formulae.

6 Claims, 6 Drawing Sheets

(51) Int. Cl.

| | |
|---|---|
| *A61B 1/05* | (2006.01) |
| *A61B 1/07* | (2006.01) |
| *H05B 33/08* | (2006.01) |
| *F21V 8/00* | (2006.01) |
| *H05B 37/02* | (2006.01) |
| *H04N 5/225* | (2006.01) |
| *G02B 23/24* | (2006.01) |
| *G02B 5/20* | (2006.01) |

(52) U.S. Cl.
CPC .............. *A61B 5/742* (2013.01); *G02B 5/201* (2013.01); *G02B 6/0008* (2013.01); *G02B 23/2469* (2013.01); *G02B 23/2484* (2013.01); *H04N 5/2256* (2013.01); *H05B 33/0815* (2013.01); *H05B 33/0842* (2013.01); *H05B 37/0227* (2013.01); *H04N 2005/2255* (2013.01)

(58) Field of Classification Search
CPC .............. G02B 23/2469; G02B 6/0008; G02B 23/2484
See application file for complete search history.

(56) References Cited

U.S. PATENT DOCUMENTS

| | | |
|---|---|---|
| 2011/0071353 A1 | 3/2011 | Ozawa et al. |
| 2012/0265041 A1 | 10/2012 | Yamaguchi et al. |
| 2013/0307106 A1 | 11/2013 | Egawa |
| 2015/0335232 A1 | 11/2015 | Ito et al. |

FOREIGN PATENT DOCUMENTS

| | | |
|---|---|---|
| JP | 2013111176 A | 6/2013 |
| JP | 2013239634 A | 11/2013 |
| JP | 2014042842 A | 3/2014 |
| JP | 2014150932 A | 8/2014 |

* cited by examiner

US 9,820,654 B2

OBSERVATION DEVICE

CROSS-REFERENCE TO RELATED APPLICATIONS

This is a continuation of International Application PCT/JP2015/079432, with an international filing date of Oct. 19, 2015, which is hereby incorporated by reference herein in its entirety. This application claims the benefit of Japanese Patent Application No. 2014-235625, the content of which is incorporated herein by reference.

TECHNICAL FIELD

The present invention relates to an observation device.

BACKGROUND ART

A special optical observation technique, such as narrow band imaging (NBI) and blue laser imaging (BLI), that facilitates detection of lesions is known. Observation according to this technique involves irradiating a observation site with narrow band light and imaging the light reflected therefrom. In white light imaging, an endoscope that uses an image sensor equipped with color filters arranged in a primary color Bayer array is used to enable simultaneous observation while maintaining excellent color reproduction.

According to this special optical observation technique, information that has entered B pixels significantly contributes to imaging of capillaries and thus B pixel information is mainly used in the display. When such observation is performed by using color filters arranged in a primary color Bayer array in which B pixels account for only one quarter of all pixels, the resolution of capillaries is insufficient.

Also known is a technique that uses G pixels having a sub-sensitivity range of the B range so that the B range information can also be obtained through G pixels. According to this technique, B information is extracted from the G pixels through image processing (for example, refer to PTL 1).

CITATION LIST

Patent Literature

{PTL 1} Japanese Unexamined Patent Application, Publication No. 2012-170639

SUMMARY OF INVENTION

Technical Problem

One aspect of the present invention provides an observation device that includes a light source unit capable of adjusting a quantity of illuminating light in a B range that spans from a wavelength of 390 nm to 490 nm according to a first B range and a second B range having a longer wavelength than the first B range; and an imaging element that images reflected light from a subject irradiated with illuminating light emitted from the light source unit. The light source unit changes a ratio of a light quantity in the first B range to a light quantity in the second B range depending on whether white light imaging is conducted or narrow band imaging is conducted, and the imaging element includes RGB color filters arranged according to pixels and the R color filter transmits more light in an R range and the first B range than light in the second B range and has a spectral characteristic that satisfies conditional formulae (1) and (2):

$$0 < Srb2/Srr \leq 0.1 \tag{1}$$

$$0.5 \leq Sbb1/Srb1 \leq 2 \tag{2}$$

Here, Srr represents sensitivity of an R pixel to the R range, Srb1 represents sensitivity of the R pixel to the first B range, Srb2 represents sensitivity of the R pixel to the second B range, and Sbb1 represents sensitivity of a B pixel to the first B range.

DESCRIPTION OF EMBODIMENTS

An observation device 1 according to a first embodiment of the present invention will now be described with reference to the drawings.

Figure 1:
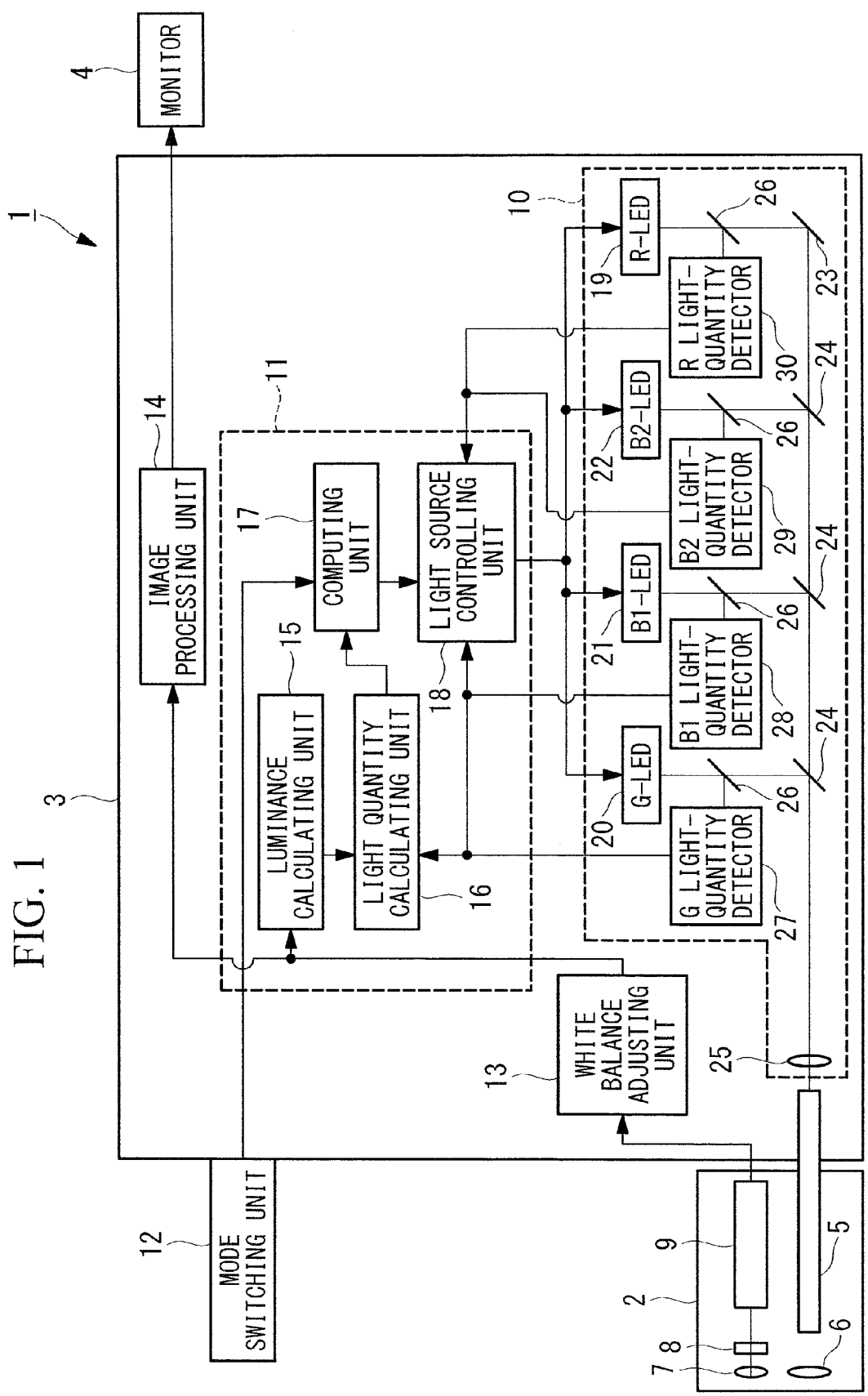
FIG. 1 is an overall view of an observation device according to a first embodiment of the present invention.

The observation device 1 according to this embodiment is, for example, an endoscopic device and, as illustrated in FIG. 1, includes a long, thin insertion portion 2 to be inserted into the body, a device main system 3 connected to a proximal end side of the insertion portion 2, and a monitor 4.

The insertion portion 2 includes an optical fiber 5 that extends through almost the entire length in the longitudinal direction to guide illuminating light, an illuminating lens 6 that emits, from a distal end of the insertion portion 2, the illuminating light that has been guided through the optical fiber 5, an objective lens 7 that collects reflected light from the imaging subject in the body irradiated with the illuminating light, and an imaging element 8 that images the light collected by the objective lens 7. The insertion portion 2 also includes an A/D converter 9 that performs A/D conversion of image signals obtained by the imaging element 8.

Figure 2:
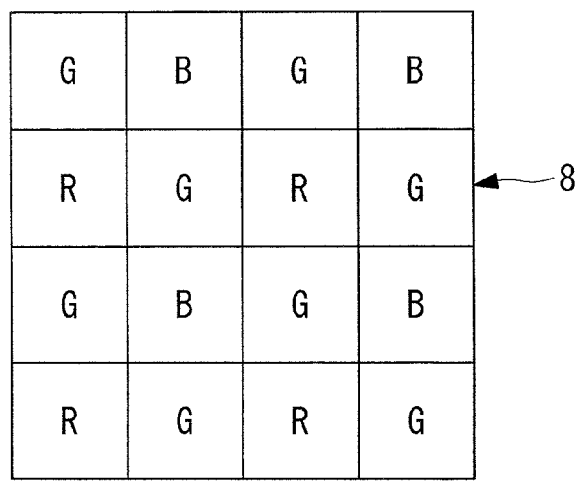
FIG. 2 is a diagram illustrating RGB color filters arranged in a Bayer array in an imaging element of the observation device shown in FIG. 1.
Figure 3:
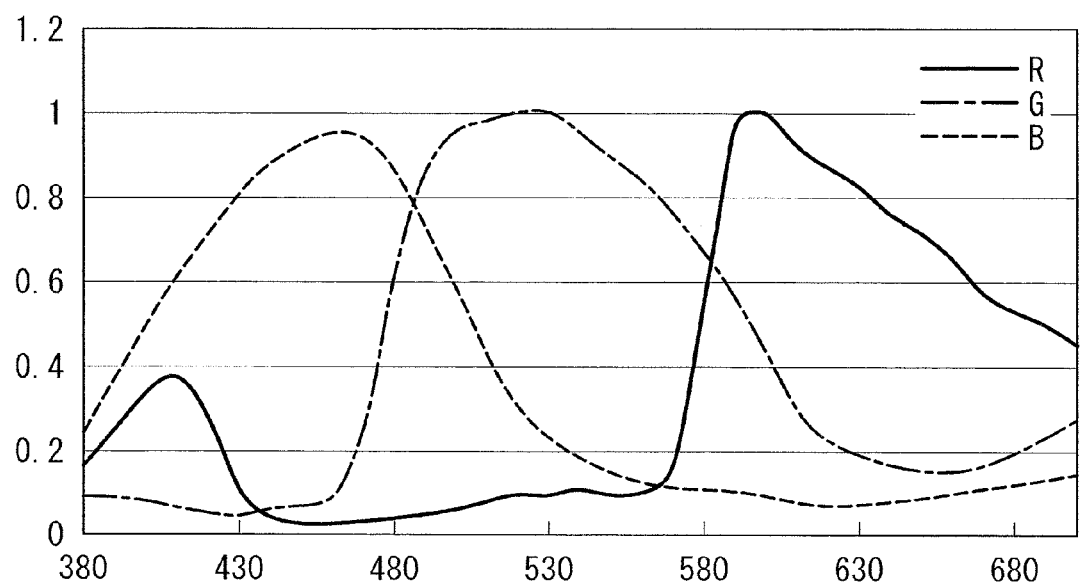
FIG. 3 is a graph showing spectral sensitivities of the imaging element shown in FIG. 2 to R, G, and B ranges.

For example, as illustrated in FIG. 2, the imaging element 8 is a CCD equipped with RGB color filters. The color filters are arranged into a Bayer array in which four pixels arranged two-by-two in the imaging element 8 include one R color filter, two G color filters, and one B color filter In this embodiment, as illustrated in FIG. 3, the R color filter has a wavelength characteristic that allows more light in the R range and the first B range described below to be transmitted than light in the second B range described below. The imaging element 8 satisfies the following conditional formulae:

$$0 < Srb2/Srr \leq 0.1 \quad (1)$$

$$0.5 \leq Sbb1/Srb1 \leq 2 \quad (2)$$

$$Srb1/Srb2 \geq 3 \quad (3)$$

Here, Srr denotes the sensitivity of an R pixel to the R range, Srb1 denotes the sensitivity of the R pixel to the first B range, Srb2 denotes the sensitivity of the R pixel to the second B range described below, and Sbb1 denotes the sensitivity of a B pixel to the first B range.

As illustrated in FIG. 1, the device main system 3 includes a light source unit 10 that emits illuminating light and a controller unit 11 that controls the light source unit 10.

The device main system 3 also includes a mode switching unit 12 that selects the observation mode between white light imaging and narrow band imaging, a white balance adjusting unit 13 that adjusts white balance for the image signal output from the A/D converter 9 of the insertion portion 2, and an image processing unit 14 that processes the image signal whose white balance has been adjusted so as to generate an observation image and output the observation image to the monitor 4.

The controller unit 11 includes a luminance calculating unit 15 that calculates an average luminance value from an image signal output from the white balance adjusting unit 13; a light quantity calculating unit 16 that calculates a target light quantity on the basis of the average luminance value calculated by the luminance calculating unit 15 and present light quantity information detected from the light source unit 10; a computing unit 17 that computes a wavelength characteristic of illuminating light to be emitted from the light source unit 10, the computation being carried out on the basis of the target light quantity calculated by the light quantity calculating unit 16 and the observation mode selected through the mode switching unit 12; and a light source controlling unit 18 that supplies electric current to the light source unit 10 according to the wavelength characteristic calculated by the computing unit 17.

As illustrated in FIG. 1, the light source unit 10 includes an R-LED (solid-state illuminating element) 19, a G-LED (solid-state illuminating element) 20, a B1-LED (solid-state illuminating element) 21, a B2-LED (solid-state illuminating element) 22, a mirror 23 and dichroic mirrors 24 that combine the illuminating light emitted from these LEDs (hereinafter may be simply referred to as solid-state illuminating elements), and a condensing lens 25 that condenses the combined white illuminating light at the input end of the optical fiber 5 so as to introduce the combined white illuminating light into the optical fiber 5.

Figure 4:
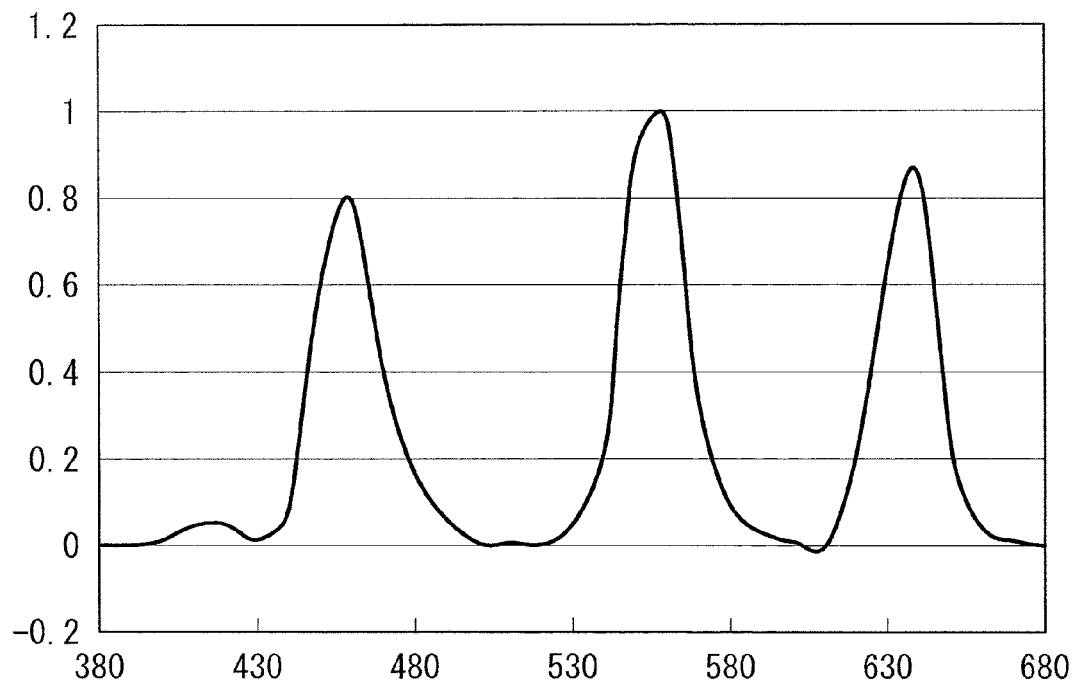
FIG. 4 is a graph showing a wavelength characteristic of a light source of the observation device shown in FIG. 1 during white light imaging.
Figure 5:
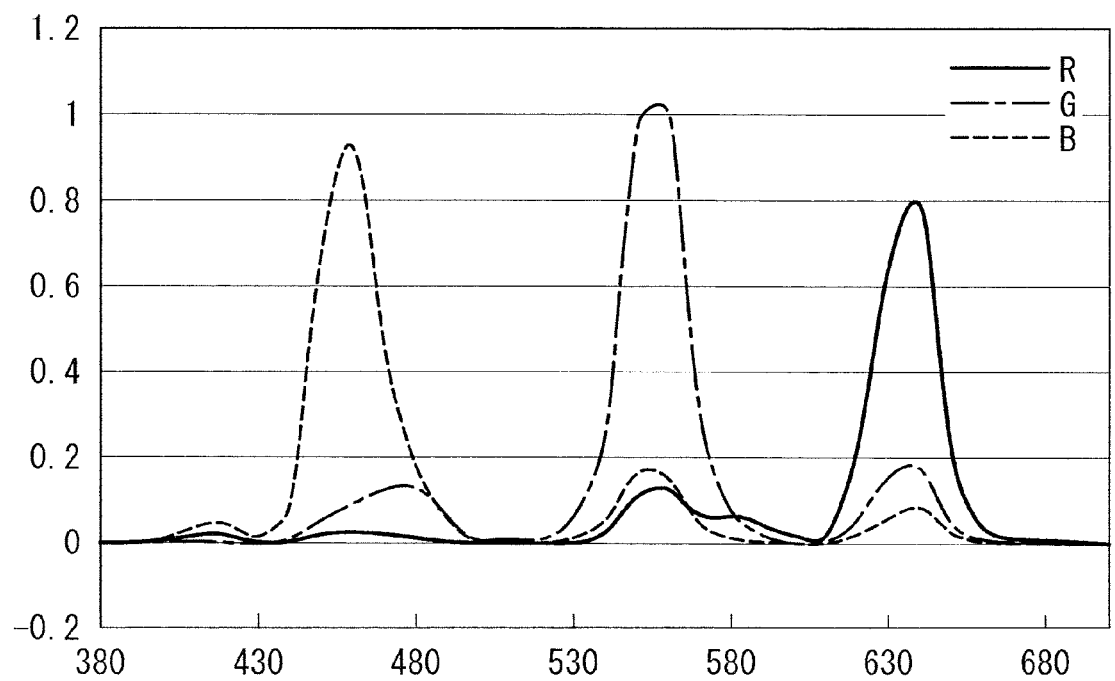
FIG. 5 is a graph in which the spectral sensitivities shown in FIG. 3 and the wavelength characteristic shown in FIG. 4 are combined.

As illustrated in FIGS. 4 and 5, the R-LED 19 emits light having a peak in the R range (from 580 nm to 650 nm), the G-LED 20 emits light having a peak in the G range (from 530 nm to 580 nm), the B1-LED 21 emits light having a peak in the B1 range (first B range: from 390 nm to 440 nm), and the B2-LED 22 emits light having a peak in the B2 range (second B range: from 440 nm to 490 nm).

As illustrated in FIG. 1, the light source unit 10 includes half mirrors 26 that split off a portion of the illuminating light emitted from the LEDs 19, 20, 21, and 22, and light-quantity detectors 27, 28, 29, and 30 that detect the quantity of the illuminating light split off by the half mirrors 26. The light quantity information detected by the light-quantity detectors 27, 28, 29, and 30 are fed back to the light source controlling unit 18 so that the information can be used in controlling the electric current. The light quantity information regarding the illuminating light emitted from G-LED 20 serves as present light quantity information and is also sent to the light quantity calculating unit 16.

A target luminance value is set in the light quantity calculating unit 16. The light quantity calculating unit 16 is configured to calculate the ratio of the average luminance value calculated by the luminance calculating unit 15 to the target luminance value and to calculate the target light quantity by multiplying the light quantity information sent from the light source unit 10 by reciprocals of the calculated ratio and the splitting ratio at the half mirror 26.

The computing unit 17 stores information regarding the light quantity ratios for the LEDs 19, 20, 21, and 22 according to the observation mode and is configured to select the information regarding the light quantity ratio corresponding to the observation mode upon receiving the information regarding the observation mode selected by the mode switching unit 12 and to calculate the light quantities for the LEDs 19, 20, 21, and 22 by referring to the target light quantity calculated by the light quantity calculating unit 16.

Specifically, the computing unit 17 is configured to cause each of the LEDs 19, 20, 21, and 22 to emit light so that light quantity ratios satisfy the following conditional formula during narrow band imaging and white light imaging:

$$Lnb2/Lnb1 < Lwb2/Lwb1 \quad (4)$$

Here, Lnb1 represents the light quantity in the B1 range of the light source unit 10 during narrow band imaging, Lnb2 represents the light quantity in the B2 range of the light source unit 10 during narrow band imaging, Lwb1 represents the light quantity in the B1 range of the light source unit 10 during white light imaging, and Lwb2 represents the light quantity in the B2 range of the light source unit 10 during white light imaging.

Operation of the observation device 1 according to this embodiment having such a structure will now be described.

In order to carry out observation by using the observation device 1 according to this embodiment, first, the insertion portion 2 is inserted into the body, and the distal end of the insertion portion 2 is arranged to oppose the observation site. While the distal end of the insertion portion 2 opposes the observation site, the user selects the observation mode through the mode switching unit 12. When white light imaging or narrow band imaging is selected as the observation mode, the information regarding the selected observation mode is sent to the computing unit 17. The initial value of the target light quantity corresponding to the target luminance value stored in the light quantity calculating unit 16 is output to the computing unit 17.

In the computing unit 17, the information regarding the light quantity ratios for the LEDs 19, 20, 21, and 22 corresponding to the observation mode sent from the mode switching unit 12 and the target light quantity input from the light quantity calculating unit 16 are used to calculate the light quantities for the LEDs 19, 20, 21, and 22, and the calculated light quantities are sent to the light source controlling unit 18. In the light source controlling unit 18, the current values to be supplied to the respective LEDs 19, 20, 21, and 22 corresponding to the input light quantities are calculated, and the LEDs 19, 20, 21, and 22 are driven.

Specifically, when white light imaging is selected as the observation mode, as illustrated in FIG. 4, the R-LED 19, the G-LED 20, and the B2-LED 22 are driven. The light in the R range, the light in the G range, and the light in the B2 range are combined through the dichroic mirrors 24 and the mirror 23 into white light, and the white light is guided to the distal end of the insertion portion 2 through the optical fiber 5 so as to illuminate the affected site through the illuminating lens 6.

During this process, portions of the light emitted from the R-LED 19, G-LED 20, and B2-LED 22 are split off by the half mirrors 26 and detected with the light-quantity detectors 27, 28, 29, and 30, and feedback is made to the light source controlling unit 18. Thus, light with a stable light quantity can be applied. The light quantity information of the light emitted from the G-LED 20 is sent to the light quantity calculating unit 16.

A portion of the illuminating light illuminating the affected site through the illuminating lens 6 is reflected at the imaging subject, is collected by the objective lens 7, and is imaged by the imaging element 8. The image information acquired by the imaging element 8 undergoes A/D conversion in the A/D converter 9 and is sent to the device main system 3.

In the device main system 3, the image information is processed in the white balance adjusting unit 13 to adjust the white balance and then sent to the image processing unit 14 and the luminance calculating unit 15. The image information is image-processed in the image processing unit 14 so as to generate an observation image. The generated observation image is sent to and displayed in the monitor 4. As a result, an user can observe the observation subject site in the body through the observation image displayed in the monitor 4.

Meanwhile, the luminance calculating unit 15 processes the image information received, calculates the average luminance value, and sends the result to the light quantity calculating unit 16. In the light quantity calculating unit 16, the ratio of the target luminance value stored therein to the average luminance value calculated in the luminance calculating unit 15 is calculated, and the actual quantity of light emitted from the G-LED 20 and sent from the G light-quantity detector 27 is multiplied by the calculated ratio so as to determine the target light quantity.

These steps are repeated at a particular sampling cycle so that the light quantity in the illuminating light emitted from the light source unit 10 is automatically adjusted, and appropriate white light imaging can be conducted.

In this embodiment, the R color filters installed in the imaging element 8 have a wavelength characteristic that allows more light in the R range and B1 range to pass through compared with light in the B2 range; however, since the illuminating light in the B range is limited to light in the B2 range, R pixels of the imaging element 8 do not detect the light in the B range as a signal as illustrated n FIG. 5 and thus color reproducibility during white light imaging can be improved.

In other words, when the conditional formula (1) is set to be greater than 0.1, the R pixels acquire sensitivity to the B-range during white light imaging, and thus color reproducibility is degraded. According to this embodiment in which the conditional formula (1) is satisfied, color reproducibility during white light imaging is improved, which is an advantage.

Figure 6:
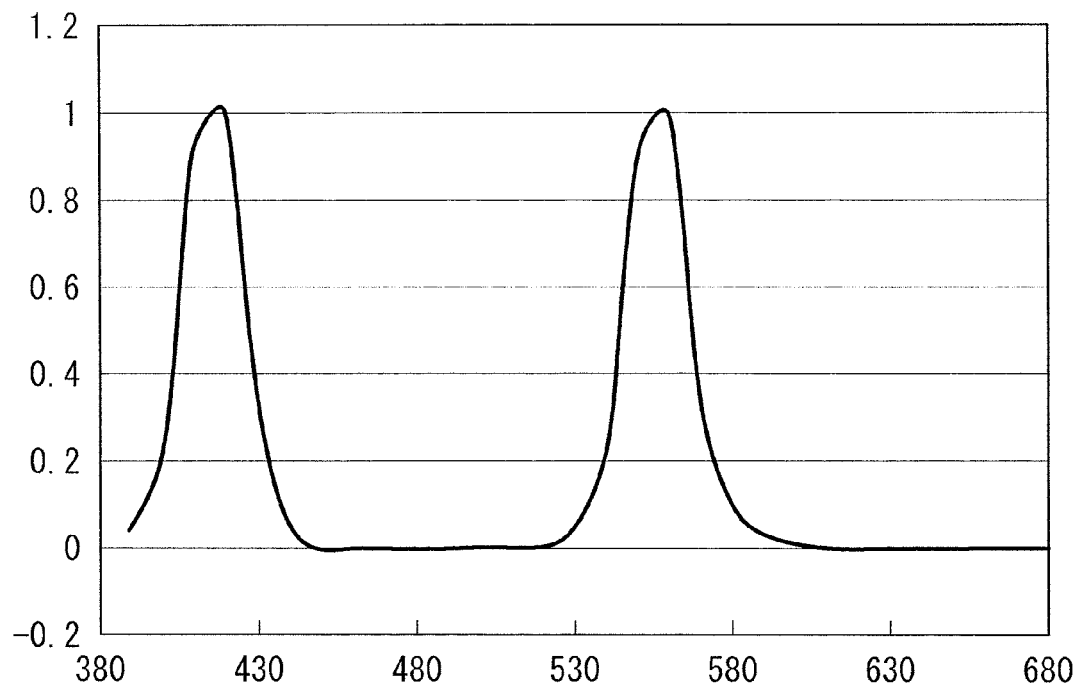
FIG. 6 is a graph showing a wavelength characteristic of a light source of the observation device shown in FIG. 1 during narrow band imaging.
Figure 7:
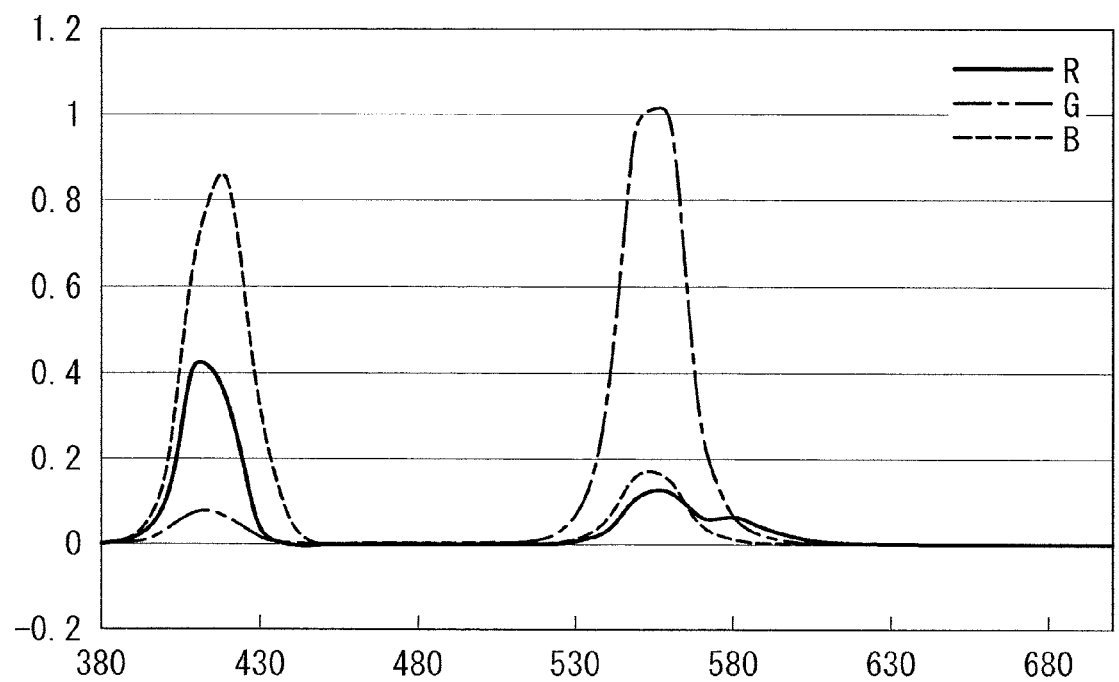
FIG. 7 is a graph in which the spectral sensitivities shown in FIG. 3 and the wavelength characteristic shown in FIG. 6 are combined.

During narrow band imaging, as illustrated in FIG. 6, the G-LED 20 and the B1-LED 21 are driven. In this case, because the R color filters installed in the imaging element 8 have a wavelength characteristic that allows more light in the B1 range to be transmitted than light in the B2 range, the illuminating light in the B1 range is detected not only by the B pixels but also by the R pixels of the imaging element 8, as illustrated in FIG. 7. Thus, more information regarding the superficial blood vessels can be acquired and, during white light imaging, the B pixels can exhibit high sensitivity to the B range, which is an advantage.

When the conditional formula (2) is set to be smaller than 0.5 or larger than 2, a difference in signal is generated between the R pixel and the B pixel during narrow band imaging and a gain must be applied to the pixel values in order to adjust the difference. As a result, the image is deteriorated due to noise and the like. According to this embodiment in which the conditional formula (2) is satisfied, deterioration of the image due to noise can be reduced, which is an advantage.

When the conditional formula (3) is set to be smaller than 3, it becomes difficult to achieve both color reproduction during white light imaging and resolution during narrow band imaging. However, in this embodiment in which the conditional formula (3) is set to be 3 or more, both can be easily achieved.

As shown by the conditional formula (4), the ratios of the light quantity in the light source unit 10 in the B2 range to that in the B1 range during white light imaging and during narrow band imaging satisfy a magnitude relationship; thus, the B-range component of the R pixels can be decreased during white light imaging compared to during narrow band imaging, and color reproduction can be improved. During narrow band imaging, the B-range component of the R pixels can be increased compared to during the white light imaging and the resolution can be improved, which is an advantage.

Next, an observation device 31 according to a second embodiment of the present invention is described with reference to the drawings.

In the description of this embodiment, parts that are common to the structure of the observation device 1 according to the first embodiment described above are denoted by the same reference numerals and descriptions therefor are omitted.

Figure 8:
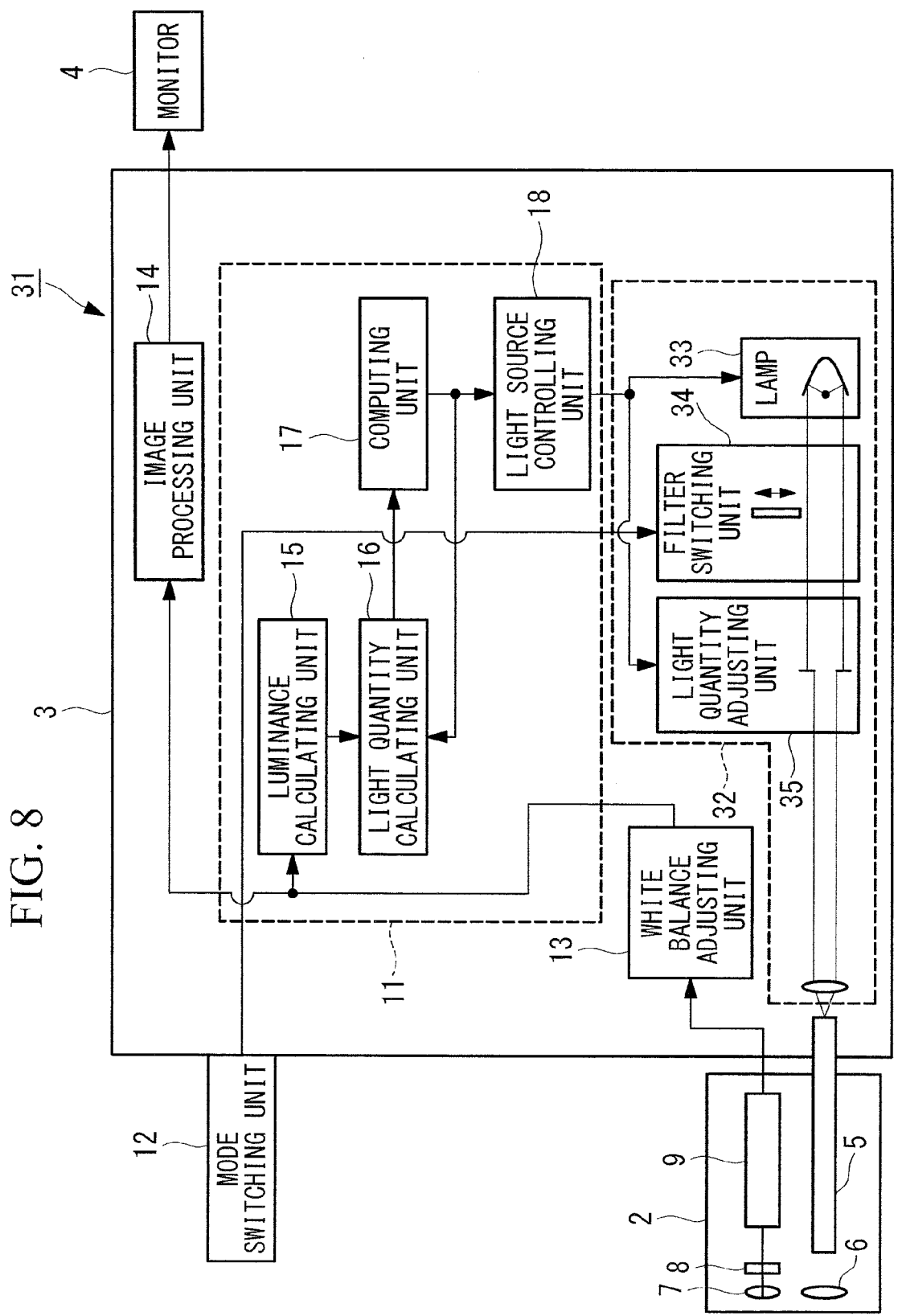
FIG. 8 is an overall view of an observation device according to a second embodiment of the present invention.

As illustrated in FIG. 8, the observation device 31 according to this embodiment differs from the observation device 1 according to the first embodiment in that a light source unit 32 includes a lamp 33 instead of the LEDs 19, 20, 21, and 22, a filter switching unit 34, and a light quantity adjusting unit 35.

Figure 9:
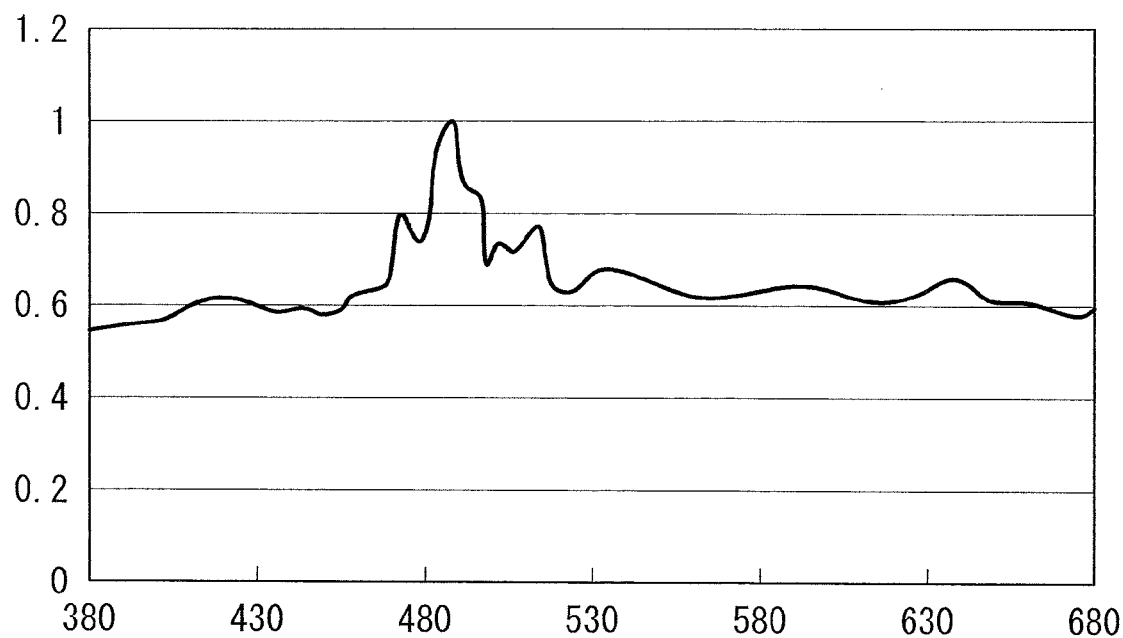
FIG. 9 is a graph showing a wavelength characteristic of a light source of a lamp of the observation device shown in FIG. 8.
Figure 10:
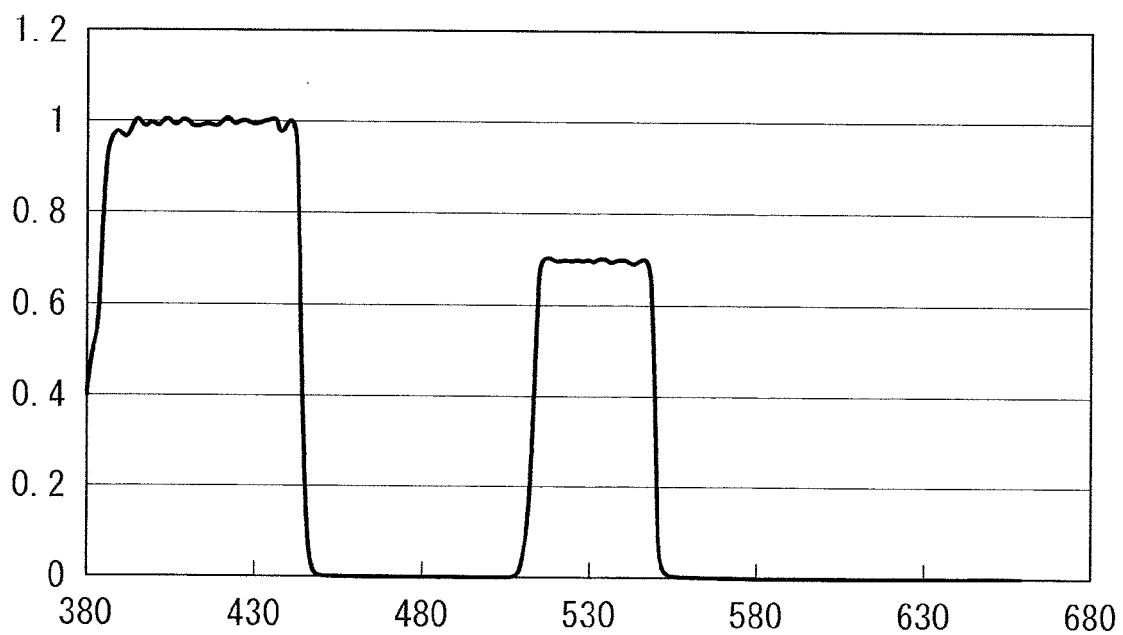
FIG. 10 is a graph showing a transmittance characteristic of a filter of the observation device shown in FIG. 8 during narrow band imaging.

The lamp 33 emits light having a broad wavelength band, as shown in FIG. 9, and is, for example, a xenon lamp. The filter switching unit 34 includes a filter for white light imaging and a filter for narrow band imaging, which are switchable. The filter for white light imaging has a wavelength characteristic that allows transmission of light in the R range, the G range, and the B2 range only. The filter for narrow band imaging has a wavelength characteristic that allows transmission of light in the G range and B1 range only, as shown in FIG. 10.

The light quantity adjusting unit 35 is, for example, a variable aperture. The information regarding the observation mode selected in the mode switching unit 12 is sent to the filter switching unit 34, and the filter suitable for the observation mode is selected and inserted in the optical path from the lamp 33. A signal is sent from the light source controlling unit 18 to the lamp 33 and the light quantity adjusting unit 35. The quantity of light emitted from the lamp 33 is roughly adjusted by adjusting the amount of electric current supplied to the lamp 33, and the opening of the light quantity adjusting unit 35 is adjusted so that the quantity of light emitted toward the optical fiber 5 can be finely adjusted.

In this embodiment, the target light quantity is calculated by feeding back, to the light quantity calculating unit 16, the light quantity command value sent from the computing unit 17 to the light source controlling unit 18 and the adjustment information (for example, the information regarding opening of the variable aperture) of the light quantity adjusting unit 35.

With the observation device 31 according to this embodiment configured in this way, once the observation mode is selected in the mode switching unit 12, the filter suitable for that observation mode is selected in the filter switching unit 34 and is placed on the optical axis from the lamp 33. Then the computing unit 17 calculates the light quantity command value for the light source controlling unit 18 and the adjustment information of the light quantity adjusting unit 35. The lamp 33 and the light quantity adjusting unit 35 are controlled by the light source controlling unit 18 on the basis of the light quantity command value and the adjustment information.

In such a case, when white light imaging is selected, a filter having a wavelength characteristic that allows transmission of light in the R range, the G range, and the B2 range only is selected. Thus, even when the R color filters installed in the imaging element 8 have a wavelength characteristic that allows transmission of light in the R range and the B1 range, the light in the B range applied is limited to the light in the B2 range and thus the R pixels of the imaging element 8 do not detect light in the B range emitted from the lamp 33. Thus, color reproducibility during white light imaging can be improved.

In contrast, during narrow band imaging, as illustrated in FIG. 10, a filter that allows transmission of light in the G range and the B1 range only is selected. In this case also, the R color filters installed in the imaging element 8 have a wavelength characteristic that allows transmission of light in the R range and the B1 range and thus the applied light in the B1 range is detected with not only the B pixels but also R pixels of the imaging element 8. Thus, compared to when detection is conducted with only the B pixels, the number of which is small in the Bayer array, more information regarding the superficial blood vessels can be obtained, which is an advantage.

Note that in the embodiments described above, the R color filters installed in the imaging element 8 have been described as blocking the light in the B2 range. However, the R color filters are not limited to ones that completely block the light in the B2 range, and the case in which the R color filters sufficiently decrease the amount of light in the B2 range compared to the light in the B1 range is also included in the scope of the present invention.

In these embodiments, the imaging element 8 that includes color filters arranged in a Bayer array has been described as an example but this is not limiting. Any other desired filter array may be employed.

As a result, the above-described embodiments lead to the following aspects.

One aspect of the present invention provides an observation device that includes a light source unit capable of adjusting a quantity of illuminating light in a B range that spans from a wavelength of 390 nm to 490 nm according to a first B range and a second B range having a longer wavelength than the first B range; and an imaging element that images reflected light from a subject irradiated with illuminating light emitted from the light source unit. The light source unit changes a ratio of a light quantity in the first B range to a light quantity in the second B range depending on whether white light imaging is conducted or narrow band imaging is conducted, and the imaging element includes RGB color filters arranged according to pixels and the R color filter transmits more light in an R range and the first B range than light in the second B range and has a spectral characteristic that satisfies conditional formulae (1) and (2):

$$0 < Srb2/Srr \leq 0.1 \quad (1)$$

$$0.5 \leq Sbb1/Srb1 \leq 2 \quad (2)$$

Here, $Srr$ represents sensitivity of an R pixel to the R range, $Srb1$ represents sensitivity of the R pixel to the first B range, $Srb2$ represents sensitivity of the R pixel to the second B range, and $Sbb1$ represents sensitivity of a B pixel to the first B range.

According to this aspect, a pixel with an R color filter (hereinafter this pixel is referred to as an R pixel) has high sensitivity to the first B range but low sensitivity to the second B range. Thus, during white light imaging, the light source unit is adjusted so that the illuminating light component of the first B range is zero or weaker than the illuminating light component of the second B range. As a result, the R pixel mainly exhibits sensitivity to the R range and thus an image whose colors are reproduced as with an imaging element equipped with a typical RGB primary color filters can be obtained.

In contrast, during narrow band imaging, the light source unit is adjusted so that the illuminating light component of the second B range is zero or weaker than the illuminating light component of the first B range. As a result, the R pixel exhibits sensitivity to the first B range as with a pixel with a B color filter (this pixel is hereinafter referred to as a B pixel). Thus, during narrow band imaging, the light of the first B range can be imaged through the R pixel and the B pixel and more information on the superficial blood vessels can be acquired.

The conditional formula (1) expresses the ratio of the sensitivity of the R pixel to the second B range to the sensitivity of the R pixel to the R range. When the conditional formula (1) is set to be greater than 0.1, the R pixels exhibit sensitivity to the B range during white light imaging and thus color reproducibility is degraded. Satisfying the conditional formula (1) can improve color reproducibility.

The conditional formula (2) expresses the ratio of the sensitivity of the B pixel to the first B range to the sensitivity of the R pixel to the first B range. When the conditional formula (2) is set to be smaller than 0.5 or larger than 2, a difference in signal between the R pixel and the B pixel is generated during narrow band imaging and a gain must be applied to the pixel values to adjust the difference. As a result, the image is deteriorated due to noise and the like. Satisfying the conditional formula (2) can reduce deterioration of the image due to noise.

In the above-described aspect, the imaging element may satisfy conditional formula (3):

$$Srb1/Srb2 \geq 3 \quad (3)$$

The conditional formula (3) expresses the sensitivity of the R pixel to the first B range relative to the sensitivity of the R pixel to the second B range. When the conditional formula (3) is set to be smaller than 3, it becomes difficult to achieve both color reproduction during white light imaging and resolution during narrow band imaging.

In the aspect described above, the first B range may be a wavelength range of 390 nm or more and less than 440 nm and the second B range may be a wavelength range of 440 nm or more and less than 490 nm.

In this manner, during narrow band imaging, resolution information of superficial blood vessels can be acquired through the R pixel and during white light imaging, the B pixel can have high sensitivity to the B range.

In the aspect described above, the color filters may be arranged into a Bayer array.

In this manner, an imaging element having a typical structure in which the transmittance characteristics of the R color filter are sophisticated can be employed.

In the aspect described above, the light source unit may satisfy conditional formula (4):

$$Lnb2/Lnb1 < Lwb2/Lwb1 \qquad (4)$$

Here, Lnb1 represents a light quantity in the first B range of the light source unit during narrow band imaging, Lnb2 represents a light quantity in the second B range of the light source unit during narrow band imaging, Lwb1 represents a light quantity in the first B range of the light source unit during white light imaging, and Lwb2 represents a light quantity in the second B range of the light source unit during white light imaging.

The conditional formula (4) expresses the magnitude relationship between the ratio of the light quantity in the second B range to the light quantity in the first B range of the light source unit during narrow band imaging and the ratio of the light quantity in the second B range to the light quantity in the first B range during white light imaging. When the conditional formula (4) is satisfied, the B range component of the R pixel can be decreased during white light imaging compared to during narrow band imaging and color reproduction can be improved. During narrow band imaging, the B range component of the R pixel can be increased compared to during white light imaging and thus the perception of resolution can be improved.

In the aspect described above, the light source unit may include at least one solid-state illuminating element having a peak in the first B range and at least one solid-state illuminating element having a peak in the second B range.

In this manner, the quantity of light in the first B range and that in the second B range can be independently controlled.

In the aspect described above, the light source unit may include a solid-state illuminating element that has a peak at a wavelength of 580 nm to 650 nm.

In this manner, the quantity of the light in the R range can be independently controlled. As a result, the R range component of the R pixel can be increased during white light imaging, and the first B range component can be increased and the R range component can be decreased during narrow band imaging.

The present invention has an advantageous effect in that the resolution of superficial blood vessels during narrow band imaging can be improved while maintaining excellent color reproducibility during white light imaging.

REFERENCE SIGNS LIST 1,31 observation device
8 imaging element
10,32 light source unit
19 R-LED (solid-state illuminating element)
20 G-LED (solid-state illuminating element)
21 B1-LED (solid-state illuminating element)
22 B2-LED (solid-state illuminating element)

The invention claimed is:

1. An observation device comprising:
   a light source unit capable of adjusting a quantity of illuminating light in a B range that spans from a wavelength of 390 nm to 490 nm according to a first B range and a second B range having a longer wavelength than the first B range; and
   an imaging element that images reflected light from a subject irradiated with illuminating light emitted from the light source unit,
   wherein the light source unit changes a ratio of a light quantity in the first B range to a light quantity in the second B range depending on whether white light imaging is conducted or narrow band imaging is conducted, and satisfies conditional formula (4), and
   the imaging element includes RGB color filters arranged according to pixels, and the R color filter transmits more light in an R range and the first B range than light in the second B range and has a spectral characteristic that satisfies conditional formulae (1) and (2):

$$0 < Srb2/Srr \leq 0.1 \qquad (1)$$

$$0.5 \leq Sbb1/Srb1 \leq 2 \qquad (2)$$

$$Lnb2/Lnb1 < Lwb2/Lwb1 \qquad (4)$$

where:
   Srr represents sensitivity of an R pixel to the R range,
   Srb1 represents sensitivity of the R pixel to the first B range,
   Srb2 represents sensitivity of the R pixel to the second B range,
   Sbb1 represents sensitivity of a B pixel to the first B range,
   Lnb1 represents a light quantity in the first B range of the light source unit during narrow band imaging,
   Lnb2 represents a light quantity in the second B range of the light source unit during narrow band imaging,
   Lwb1 represents a light quantity in the first B range of the light source unit during white light imaging, and
   Lwb2 represents a light quantity in the second B range of the light source unit during white light imaging.

2. The observation device according to claim 1, wherein the imaging element satisfies conditional formula (3):

$$Srb1/Srb2 \geq 3 \qquad (3).$$

3. The observation device according to claim 1, wherein the first B range is a wavelength range of 390 nm or more and less than 440 nm, and
   the second B range is a wavelength range of 440 nm or more and less than 490 nm.

4. The observation device according to claim 1, wherein the color filters are arranged in a Bayer array.

5. The observation device according to claim 1, wherein the light source unit includes at least one solid-state illuminating element having a peak in the first B range and at least one solid-state illuminating element having a peak in the second B range.

6. The observation device according to claim 1, wherein the light source unit includes a solid-state illuminating element that has a peak at a wavelength of 580 nm to 650 nm.

* * * * *